United States Patent [19]
Wilhoit

[11] Patent Number: 5,771,514
[45] Date of Patent: Jun. 30, 1998

[54] ADJUSTABLE CONTOUR PILLOW

[75] Inventor: Christopher S. Wilhoit, Columbia, Tenn.

[73] Assignee: Chris Wilhoit, Columbia, Tenn.

[21] Appl. No.: 676,462

[22] Filed: Jul. 8, 1996

[51] Int. Cl.$^6$ ........................................ A47G 9/00
[52] U.S. Cl. ........................................ 5/644; 5/421
[58] Field of Search ................ 5/644, 636, 708, 5/654, 713, 421, 915; 297/180.11, 284.1

[56] References Cited

U.S. PATENT DOCUMENTS

| | | | |
|---|---|---|---|
| 795,108 | 7/1905 | Doellinger | 5/644 |
| 3,411,164 | 11/1968 | Sumergrade | 5/644 |
| 4,501,034 | 2/1985 | Greenawalt | 5/644 |
| 4,805,603 | 2/1989 | Cumberland | 5/644 |
| 4,914,766 | 4/1990 | Moore | 5/644 |
| 5,068,933 | 12/1991 | Sexton | 5/644 |
| 5,406,661 | 4/1995 | Pekar | 5/654 |
| 5,586,347 | 12/1996 | Frischknecht | 5/708 |

FOREIGN PATENT DOCUMENTS

| 2648999 | 1/1991 | France | 5/644 |
|---|---|---|---|

*Primary Examiner*—Alexander Grosz
*Attorney, Agent, or Firm*—Litman Law Offices; Dolph Torrence

[57] ABSTRACT

An adjustable contour pillow provides for the manual or powered inflation of the chamber or chambers therein, as well as other alternative features such as heat, massage, and/or cooling, and is particularly valuable to persons suffering from neck strain. In one embodiment, the pillow includes three separate laterally disposed elongate fluid chambers, each having a coplanar lower wall. The central chamber has a center and an upper wall which is lower than the centers and upper walls of the other two chambers, thus defining an elongate valley extending from one end to the other of the pillow. The valley serves to cradle the back of the head, with the uppermost chamber (relative to the user) cradling the upper back of the head and the lowermost chamber supporting the back of the neck of a supine person. The selective and independent inflation of the different chambers may be accomplished manually, or by an automated powered pump arrangement. The control system may be integrated with the pillow, or may alternatively be supplied as a separate control for a pillow having one or more inflatable chambers therein.

7 Claims, 3 Drawing Sheets

ADJUSTABLE CONTOUR PILLOW

BACKGROUND OF THE INVENTION

1. Field of the Invention

The present invention relates generally to pillows, rests, and the like for the support of the head and neck of a reclining person, and more specifically to an adjustable pillow having at least one adjustably inflatable chamber therein. The inflation medium may comprise air or another fluid. The pillow includes a control system and inflation means therefor, preferably permanently or removably integrated therewith, to control the amount of inflation adjustably as desired by the user. Additional features may be included, such as heating and/or massage means, integrated with the pillow.

2. Description of the Prior Art

Upper back and neck pain are common problems in today's world, with whiplash injuries, sports injuries, fatigue, and other causes producing innumerable cases of such pain. In many cases, proper support of the back of the head and neck while resting, can provide considerable relief from such pain by relieving the stress in the neck and upper back muscles otherwise required to support the head relative to the remainder of the body, even at rest. Accordingly, various pillows and similar supports have been developed over the years, as will be discussed further below.

However, it is important that such a pillow provide some means of adjustment, as the specific contour required for optimum comfort and support often changes over a period of time. Also, different individuals in the same family or household may find such a contour pillow to be of value at different times, and these different individuals may require different contours from one another. Also, along with the need to provide an optimum contour for different situations, it is often helpful to provide heat and/or massage to relax strained muscles further.

Accordingly, a need will be seen for an adjustable contour pillow which includes one or more adjustably inflatable chambers therein, with each of the plural chambers being independently adjustable to suit the particular needs of an individual, when more than a single chamber is provided. The chambers are preferably filled with air, but other inflation media may be used as desired (liquids or other gases). The pillow must also optionally provide heating and/or massage means, for further comfort of the user. The various controls for all of these different functions may be integrated with the pillow, and the control means may include a memory therewith, enabling different users to select a preset optimum setting of inflation pressures for multiple chambers, heat setting, and/or massage setting, as desired. A review of the distinctions between the prior art known to the inventor and the present invention is provided immediately below.

U.S. Pat. No. 3,411,164 issued to Saul Sumergrade on Nov. 19, 1968 describes a Pillow having three longitudinally disposed compartments, each filled with some soft and resilient material (down, feathers, etc.). A pneumatically inflatable chamber is optionally provided in only the central compartment, substantially centered within the resilient material; no inflation means is provided for the left and right compartments. All compartments or chambers of the present pillow are inflatable, and the compartments are laterally disposed, rather than the longitudinal disposition of the Sumergrade pillow. Moreover, the plural chamber embodiment of the present pillow provides for a lower central area of the pillow, into which the back of the head may nest, so the back of the neck is supported by a relatively higher inflatable chamber.

U.S. Pat. No. 4,501,034 issued to Monte H. Greenawalt on Feb. 26, 1985 describes an Inflatable Pillow having one or two laterally disposed adjustably inflatable bladders therein. The lowermost bladder extends from about one quarter to about three quarters of the width of the pillow, and does not extend for the entire width. No third bladder is disclosed to cradle the upper portion of the head, as provided in embodiments of the present pillow invention. Moreover, Greenawalt does not provide any powered inflation means for his pillow. Greenawalt's two pillow bladders are coplanar, which would tend to provide excessive support for the back of the head, whereas the central chamber of the present multiple chamber pillow is displaced lower than the others.

U.S. Pat. No. 4,550,459 issued to Dieter Endel et al. on Nov. 5, 1985 describes an Orthopedic Pillow comprising various configurations of two or three resiliently stuffed pillows sewn laterally together. While Endel et al. recognize the need for cervical support in their orthopedic pillow, they provide no inflation means for any of the different components of their pillow, as provided by the present invention.

U.S. Pat. No. 4,805,603 issued to Keith Cumberland on Feb. 21, 1989 describes an Inflatable Cervical Traction Pillow of two separate sections of resilient material, divided laterally along a line passing under the back of the neck of a user of the pillow. An inflatable bladder is placed between the two portions, rather than being installed within a portion of the pillow, as in the present invention. The bladder is adapted to spread the sections apart to provide a form of traction to the cervical area of the user, rather than to raise or lower one section of the pillow relative to another section, as in the present pillow.

U.S. Pat. No. 4,829,614 issued to James A. Harper on May 16, 1989 describes an Adjustable Pillow With Neck Support, wherein a series of equal size coplanar inflatable bladders are laterally disposed in a pillow having an essentially level upper surface, with an additional bladder disposed over an outermost lower bladder. The result provides neck support, but no corresponding support to cradle the top of the head is provided, as in the present pillow, which uses differently configured chambers having coplanar bases to provide the depression for the back of the head.

U.S. Pat. No. 5,367,731 issued to Dennis C. O'Sullivan on Nov. 29, 1994 describes a Therapeutic Pillow Having an Exterior Depression On One Side For Providing Different Degrees Of Support To A User's Neck. Several embodiments are disclosed, each having a central depression for the head. The raised area around the center extends entirely therearound, rather than the central depression comprising an elongate valley between two opposite raised peripheral edges, as in the multiple chamber embodiment of the present invention. In any event, the O'Sullivan pillow embodiments are each filled with a conventional resilient fill material, rather than being inflatable, as in the present pillow.

U.S. Pat. No. 5,471,691 issued to James D. Ryndak on Dec. 5, 1995 describes a Multitiered Pillow Construction, wherein a multiple compartment lower tier of essentially coplanar compartments has a pair of laterally opposed compartments thereatop. The Ryndak pillow is thus oriented ninety degrees to the present pillow, and while the Ryndak pillow does cradle the head, it provides no neck support whatsoever, as provided by the present pillow. Moreover, conventional fill is used by Ryndak; no inflation means is disclosed.

British Patent Publication No. 2,026,315 to Reginald Dyson and published on Feb. 6, 1980 describes Cushions And Mattresses having two interconnected coplanar chambers. Valve means is provided to allow fluid to move from one chamber to another, to inflate the two chambers differentially as desired. No external independent inflation is provided, as with the present invention.

Finally, French Patent Publication No. 2,648,999 to Henry Kogan and published on Jan. 4, 1991 describes an inflatable pillow or the like having three laterally disposed chambers, each of a different diameter. The central chamber has the smallest diameter, with the chamber adapted to be placed beneath the neck having an intermediate diameter. The centers of all of the chambers are coplanar, and thus the pillow is symmetrical, unlike the present pillow. Moreover, the lengths of the chambers are all different, resulting in a generally triangular shape for the Kogan pillow, whereas the present pillow has a rectangular planform. No automated inflation means or other automated features are disclosed by Kogan.

None of the above inventions and patents, taken singly or in combination, is seen to describe the instant invention as claimed.

SUMMARY OF THE INVENTION

Accordingly, it is a principal object of the invention to provide an improved adjustable contour pillow including a plurality of chambers and having vertical asymmetry, with all chambers having coplanar lower walls and a central chamber having an upper wall which is lower than the upper walls of the other chambers, thereby providing a valley for the back of the head of the user.

It is another object of the invention to provide an improved adjustable contour pillow which chambers may be manually inflated, or which may include control means providing for the selectively powered inflation of a pillow having one or more chambers.

It is a further object of the invention to provide an improved adjustable contour pillow which control means may be integrated with the pillow, or may be provided separately.

An additional object of the invention is to provide an improved adjustable contour pillow which may also include heating and massage means therein, controlled by integrated or separate control means, as well as cooling means which may be removably placed within the pillow cover.

Still another object of the invention is to provide an improved adjustable contour pillow which control means may control an individual inflation pump with selectable valve means for each chamber, or which may control individual pumps for each chamber.

Yet another object of the invention is to provide an improved adjustable contour pillow which may be inflated with air or other gas or liquid as desired.

Another of the objects of the invention is to provide an adjustable contour pillow which powered inflation, heating, and/or massage means may be powered by battery or external electrical power, as desired.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
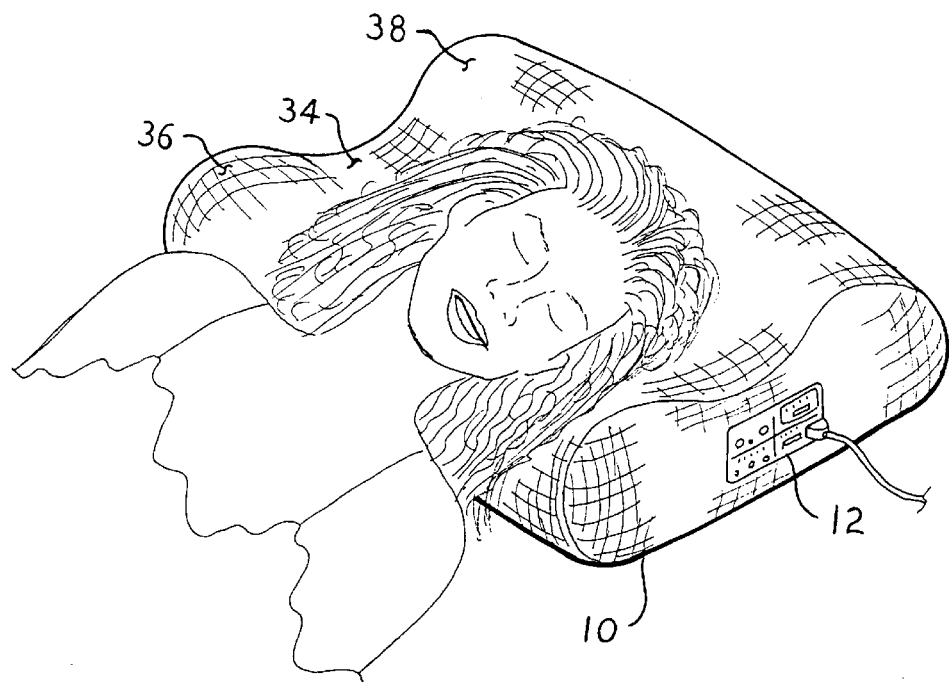
FIG. 1 is an environmental perspective view of the present adjustable contour pillow in use, and showing its general configuration.

The present invention comprises an adjustable contour pillow, generally designated with the numeral 10 in the drawing figures, and a control system 12, which may be used to control the inflation and deflation of the pillow 10, as well as to control other options (heating, massage, etc.) which may be provided with the pillow 10. FIG. 1 provides an overall view of the present pillow 10 and control system 12. While the control system 12 is shown in combination with an inflatable pillow 10 having a plurality of inflatable chambers therein, it will be understood that the control system may be used with other configurations of inflatable pillows, having one or more selectively inflatable and deflatable chambers therein.

Figure 2:
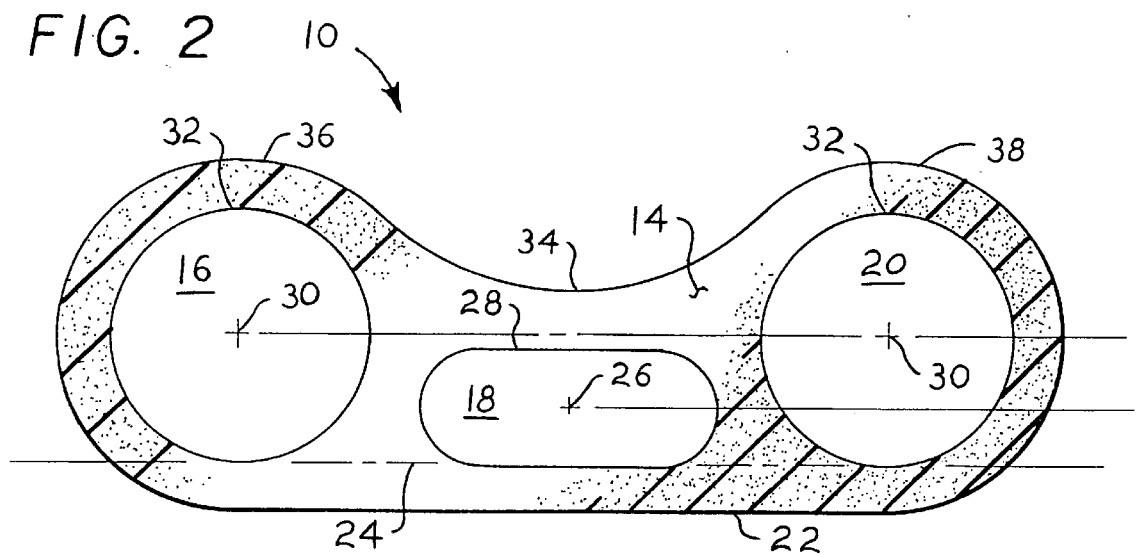
FIG. 2 is a side elevation view in section of the present adjustable contour pillow, showing the common lower wall height of each of the chambers and the lower center and upper wall of the central chamber.

A cross sectional view of the present adjustable contour pillow 10 is provided in FIG. 2. The pillow 10 generally comprises a resilient cushion 14 (open or closed cell foam, or a thin sheet covering enclosing other loose fill material, etc.) which surrounds a first, a second, and a third selectively inflatable chamber, respectively 16, 18, and 20. The three chambers 16 through 20 are separate, adjacent, parallel elongate tubes of essentially equal length, and are laterally disposed to extend the entire width of the pillow 10, and essentially define the generally rectangular planform of the adjustable contour pillow 10. Cushion material may be provided surrounding the ends of the chambers 16 through 20, if desired, or the chamber 16/18/20 ends may be exposed for access.

The first and third chambers 16 and 20 are essentially cylindrical in shape, with a circular cross section, while the second chamber 18, disposed between the other two chambers 16 and 20, is of a generally oval cross section. The lower surface 22 of the enclosing cushion 14 is essentially flat and planar, thereby defining a coplanar lower wall or surface 24 for each of the chambers 16 through 20 within the cushion 14. However, although each of the chambers 16 through 20 is of substantially equal volume, due to the fact that the central chamber 18 is of a flattened oval cross section, it will be seen that its geometric center 26, and thus its upper wall 28, is lower than the geometric centers 30 and upper walls 32 of the first and third chambers 16 and 20.

This results in the pillow 10 having an elongate central valley 34 defined by the higher cushion portions 36 and 38 respectively above the two higher cylindrical chambers 16 and 20 to each side of the lower centrally disposed oval chamber 18.

Figure 3:
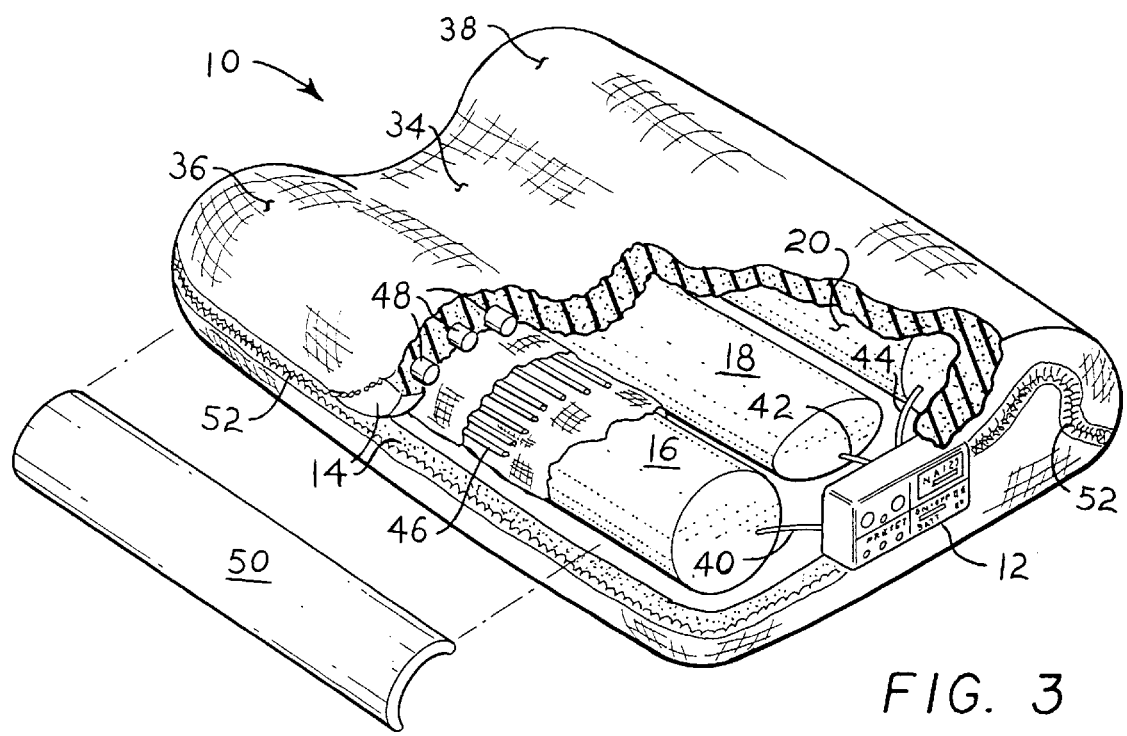
FIG. 3 is a partially broken away perspective view of the present adjustable contour pillow, showing the fluid chambers therein, the heating and massage means, and the controls therefor, as well as the removably installable cooling means therefor.

FIG. 3 provides a partially broken away perspective view of the present adjustable contour pillow 10, showing the internal structure and optional features which may be incorporated therein. The control system 12 selectively controls the independent inflation and deflation of each of the chambers 16, 18, 20, as will be discussed below, via interconnecting inflation and deflation tubes, respectively 40, 42, and 44. Air (or other gas or liquid, hereinafter described as a fluid) is selectively pumped to or from each of the chambers 16, 18, 20 by pump means, described further below, through the tubes 40, 42, and 44.

The pillow 10 and control system 12 may incorporate additional features, such as some form of electrical heating elements 46 and/or massage elements 48, as shown generally and schematically in FIG. 3 disposed above the first chamber 16 and below the corresponding cushion portion 36. The heating elements 46 may be in the form of an electrically resistive wire, as in electric blankets and the like, or other means as desired. The massage elements 48 may comprise elongate rotating or oscillating rod elements having irregular surfaces, so as to cause the cushion portion 36 to pulse or vibrate as the irregular surfaces of the massage elements 48 rotate or oscillate, or other means such as eccentrically weighted elements to cause a vibration as they rotate. These heating and/or massage elements 46 and 48 are preferably sandwiched between the first chamber 16 and overlying cushion portion 36 so as to provide heat and massage to the neck of a person using the pillow 10, but it will be seen that they may be installed within any portion of the pillow 10, as desired.

Also shown in FIG. 3 is a removably installable cooling means 50, such as a thin, flat flexible container of eutectic substance, which may be chilled and removably inserted within the pillow 10. A zipper, Velcro (tm), or other means 52 may be used to open and close the cushion 14 to provide access to the interior thereof, for insertion and removal of the cooling means 50. The cooling means 50 is adapted for placement above the first chamber 16, to underlie the neck of a user, but it will be seen that the cooling means may be removably placed in other pillow areas as well.

Figure 4:
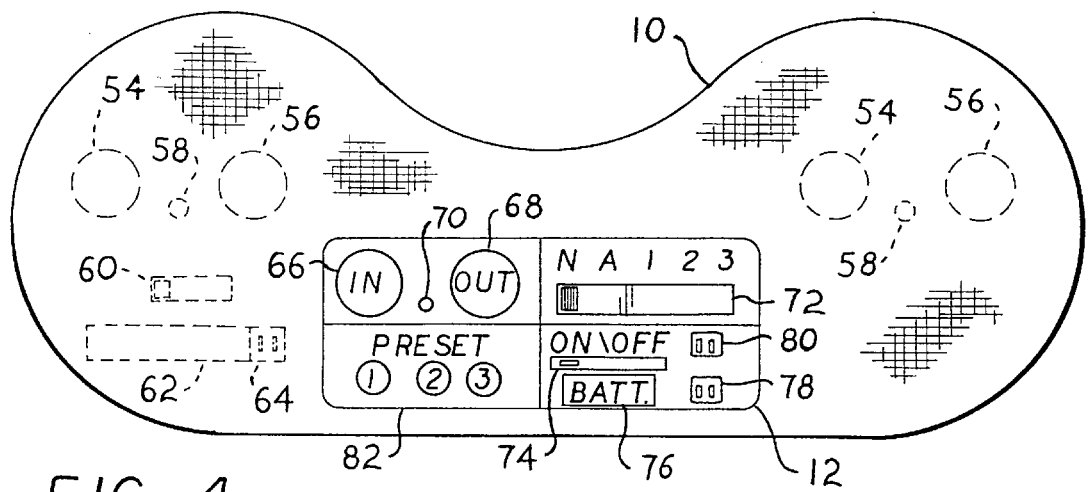
FIG. 4 is an end elevation view of the adjustable contour pillow embodiment of FIG. 3, providing a detail view of the controls therefor as well as alternative control means in broken lines.

FIG. 4 provides a detailed view of the control system 12 installed in one end of a pillow 10. (It will be seen that the control system 12 may be installed in any practicable location in the pillow 10, or may even be remotely connected thereto.) This control system 12 may be permanently integrated with the remainder of the pillow 10 and its accessories as discussed above, or may alternatively be provided as a separate, modular unit which may be incorporated later in a pillow initially equipped with manually operated controls, such as the alternative inflation and deflation buttons, 54 and 56, and fluid inlet/outlet orifice 58, shown in broken lines for the first and third chambers of the pillow 10 in FIG. 4. These manual inflation and deflation controls 54, 56 may be similar to those used with selectively inflatable cushions used in certain athletic shoes, or other manual pump means. While these manual pump means 54 and 56 are only shown for the first and third chambers of the pillow 10 in FIG. 4, it will be seen that such manual means may be used for any of the chambers of the pillow 10. Also, while these manual pump means 54 and 56 are shown for individual chambers, it will be seen that such manual means may be used for the inflation and deflation of a plurality of chambers.

The pillow 10 of FIG. 4 may include other alternative features as well, such as an electric control switch 60 to operate the heating and/or massage means 46 and 48, a battery pack 62, and/or an electrical plug 64 for connection to an external electrical power source (115 volt ac current, 12 volt converter, etc.). These features 60 through 64 are shown in broken lines, as they may be provided with a pillow 10 having manual inflation means, if desired, with the modular control system 12 being added later.

The control system 12 of FIG. 4 includes inflation and deflation buttons, respectively 66 and 68, as well as an inlet/outlet orifice 70, analogous to the manual means discussed above but controlling the inflation and deflation of multiple chambers. It will be understood that the inflation and deflation buttons, respectively 66 and 68, may also function as switches controlling the operations of electric fluid pump(s). Also, with only a single switch 66 or 68 disclosed for the inflation or deflation of any of the three chambers 16 through 20, a selector switch 72 is required. This switch 72 may be in the form of a slide switch, with positions for either the first chamber 16, the second chamber 18, or the third chamber 20, or for all chambers simultaneously ("A"), or for none of the chambers ("N"), to preclude inadvertent inflation or deflation of the chamber(s) in the event the corresponding inflation or deflation switch button 66/68 is pressed. An electrical master on/off switch 74 for all functions may also be incorporated.

The control system 12 and the various inflation, deflation, heating, and/or massage means controlled thereby may be battery powered, if desired, with a battery pack 76 being provided. Alternatively, external electrical power may be provided by means of connection to an electrical receptacle 78. An optional electrical outlet 80 may be provided to power the heating and/or massage means as desired, in the event these are added as modular components to a pillow not initially having these features installed. It should be noted that the various specific controls illustrated in FIG. 4 are exemplary, and other control locations and configurations may be used as desired, depending upon the number of additional features incorporated and other factors.

In addition to the above, modern electronics permits the addition of an inexpensive memory unit 82, which will retain inflation pressure settings, heat level, and/or massage operation settings for more than a single individual user of the present pillow 10. While three different memory settings are shown, it will be seen that more or fewer such settings may be incorporated within the present control system 12, as desired.

Figure 5:
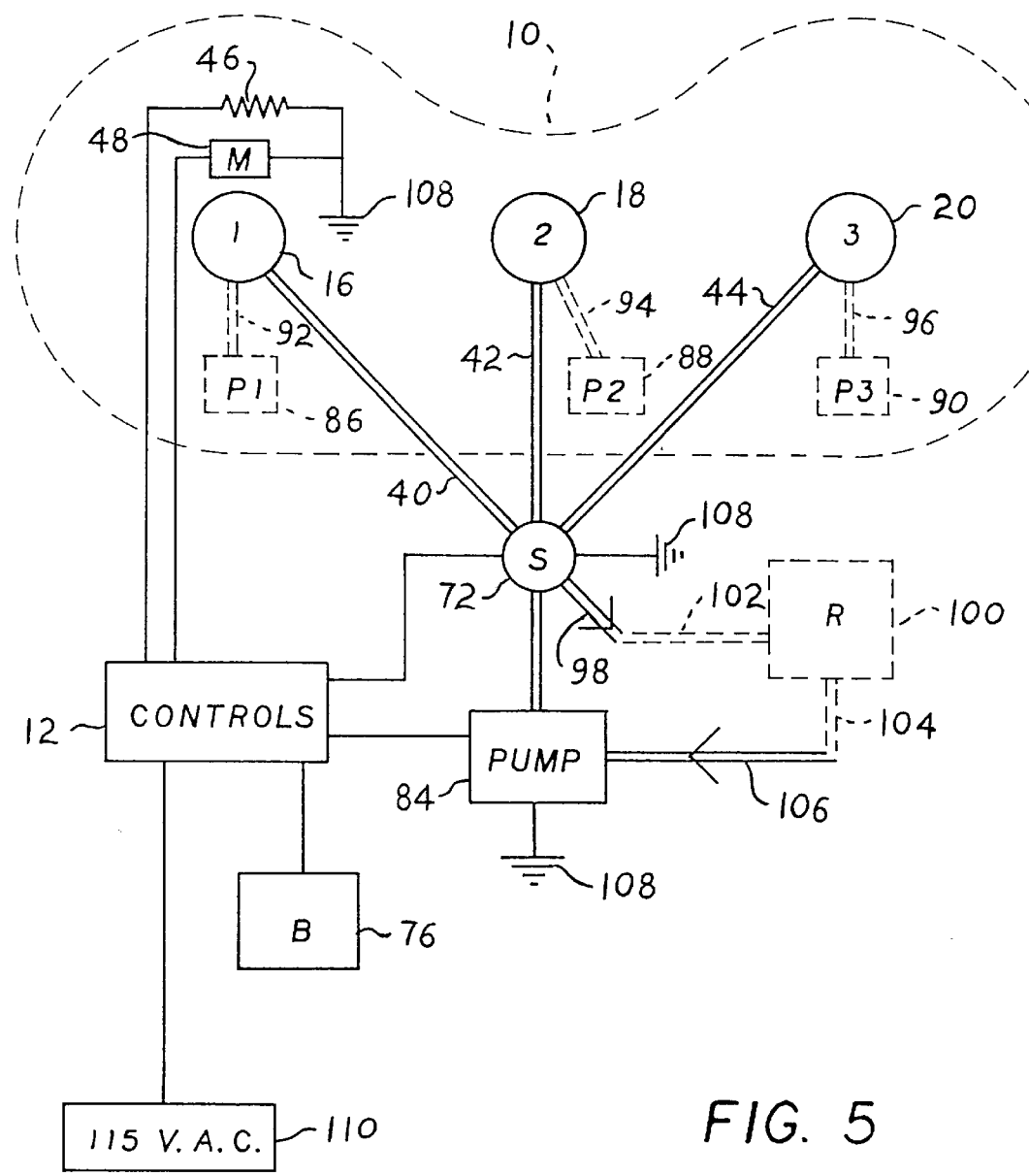
FIG. 5 is a mechanical and electrical schematic drawing of the pneumatic and electrical circuitry which may be incorporated with the present adjustable contour pillow.

FIG. 5 provides an electrical and mechanical schematic illustration of the operation of the electrical version of the present control system 12. The pillow 10 is shown in broken lines, with various components shown therein. The controls of the control system 12 are shown electrically connected to, but physically separated from, the pillow 10 and other components therein. It will be understood that the control system 12 with its various electronic switch and control means, may be integrated with the pillow 10 and other components therewith, or may alternatively be provided as a separate unit, communicating with the pillow 10 only by means of electrical and/or fluid connections, as required.

The control system 12 provides for the selective electrical activation of a pump 84, which in turn selectively inflates or deflates the first, second, and third chambers 16, 18, and 20 by means of a selector and switch 72, as shown on the illustration of the control system 12 control panel in FIG. 4. The selector 72 distributes the inflation fluid to the respective chamber(s) 16, 18, and/or 20 as selected, respectively via the first, second, and/or third chamber inflation/deflation tubes 40, 42, and/or 44.

Alternatively, the selector switch 72 may be eliminated by providing separate pumps P1 through P3, respectively designated numerically as pumps 86, 88, and 90, shown in broken lines within the pillow 10 of FIG. 5, and providing fluid to their respective chambers 16 through 20 respectively by means of fluid transfer lines or tubes 92, 94, and 96. These individual pumps 86 through 90 for each of the chambers 16 through 20 are analogous to the individual pump inflation means 54 disposed within the pillow 10 for each chamber, shown in broken lines in FIG. 4.

As noted further above, the various chambers 16, 18, and 20 of the present adjustable contour pillow 10 may also be selectively deflated, as desired. This may be accomplished by means of an outlet line 98, routed through the selector switch 72 to relieve inflation pressure within any of the chambers 16/18/20 as selected. In the event that air is used as the inflation medium, the outlet line 98 may vent to ambient atmosphere, as indicated by the solid portion of the line 98 and outlet arrow. However, in the event that another fluid is used (e.g., nitrogen gas, liquid water, etc.) then a reservoir 100, shown in broken lines, would be required, and the outlet line 98 would have a return line extension 102 to the reservoir 100. A fluid inlet line 104, also shown in broken lines, would also extend from the reservoir 100 to the pump inlet 106 in the event of a fluid (gas or liquid) other than air being used for the inflation of the chambers 16 through 20 of the present pillow 10.

The control system 12 may also provide for the selective actuation and deactivation of the heating means 46 and/or massage means 48, discussed further above and shown in FIG. 3, as desired. These various electrical elements (heating means 46, massage means 48, selector switch 72, and/or pump 84 may be interconnected by an electrical ground connection 108 establishing a common electrical potential for all of the electrical elements. As noted further above, the various electrical components of the present adjustable contour pillow 10 may be powered either by battery means 76, or alternatively by 115 volt alternating current 110 from a conventional electrical grid system, as in standard household electrical current. Such electrical power means 110 may be connected to the control system 12 for the pillow 10 by means of the electrical power receptacle 78 of FIG. 4, either directly or indirectly through a power converter (not shown) to adjust the electrical characteristics as desired.

In summary, the adjustable contour pillow 10 will be seen to provide a most desirable means of relaxing the neck muscles of a person suffering from such muscle strain. The user need only place the pillow 10 in a suitable position, provide appropriate electric power (batteries 76 or external power 110), and recline with the neck resting upon the cushion portion 36 above the first chamber 16, with the back of the head nesting in the valley 34 above the second chamber 18 and between the two higher cushion portions 36 and 38. The upper back portion of the head will thus be cradled by the higher cushion portion 38 above the third chamber 18.

The various chambers 16, 18, and 20 may be inflated or deflated selectively as desired to provide optimum comfort and support for the user of the pillow. 10, by means of the control system 12. (Manual inflation means, as described further above, may be used for pillows 10 without electrical components.) For such pillows 10 which use electrical power, the optional heating and/or massage means 46 and/or 48 may also be activated as desired, for further relaxation and comfort. In the event of a pillow 10 incorporating memory means 82, the above functions could be programmed into the memory 82, thus allowing all of the above inflation, heating, and/or massage functions to be activated as desired with the press of a single button.

The control system 12 of the present adjustable contour pillow 10 may be provided integrally with a multiple chamber pillow 10, but it will be seen that at least some components of the control system 12 lend themselves to modular incorporation with an existing pillow having one or more inflatable and deflatable chambers. Thus, the control system 12 may be provided separately, and used to provide for the selective inflation and deflation of an existing inflatable pillow, as desired. The present adjustable contour pillow 10 and its control system 12 will thus be seen to be quite adaptable, to accommodate a wide variety of users and their needs.

It is to be understood that the present invention is not limited to the sole embodiments described above, but encompasses any and all embodiments within the scope of the following claims.

I claim:

1. An adjustable contour pillow, comprising:

an adjustably inflatable pillow including a resilient cushion having a first, a second, and a third separate but adjacent elongate selectively inflatable and deflatable chamber of substantially equal volume and length therein and defining the width of said pillow, with each said chamber being laterally disposed within said cushion;

each said chamber having a lower wall mutually coplanar with one another, with said first chamber and said third chamber each having a substantially circular cross section and with said second chamber being disposed therebetween and having a substantially oval cross section and a lower geometric center than said first chamber and said second chamber, with said cushion of said pillow thereby having an upper surface defining an elongate valley between said first chamber and said third chamber and extending completely across said width of said pillow; a control system cooperating and communicating with said first, second and third chambers of said pillow, said control system adapted to provide for the selective inflation and deflation of said first, second and third chambers of said pillow as desired, said control system being removably installed in said contour pillow to communicate with said first, second and third chamber's of said pillow, with said control system being used selectively to inflate and deflate said first, second and third chambers of said pillow as desired.

2. The adjustable contour pillow of claim 1, wherein:

said first chamber is adapted to support the neck of a user of said pillow, and said second chamber is adapted to support the back of the head of a user of said pillow.

3. The adjustable contour pillow of claim 1, wherein:

said cushion includes heating means disposed below said upper surface thereof and at least over said first chamber thereof, with said heating means being selectively operable by means of said control system.

4. The adjustable contour pillow of claim 1, wherein:

said cushion includes massage means disposed below said upper surface thereof and at least over said first chamber thereof, with said massage means being selectively operable by means of said control system.

5. The adjustable contour pillow of claim 1, wherein:

said pillow includes cooling means removably insertable below said upper surface of said cushion and at least over said first chamber thereof.

6. The adjustable contour pillow of claim 1, including: memory means providing for the establishment of at least one preselected condition by said control means, as desired.

7. The adjustable contour pillow of claim 1, wherein:

said control system is battery powered.

* * * * *